United States Patent [19]

Portmann

[11] 4,189,584

[45] Feb. 19, 1980

[54] PROCESS FOR THE PRODUCTION OF 2-BROMO-3-CYANO-4,6-DIAMINOPYRIDINE

[75] Inventor: Robert Portmann, Bottmingen, Switzerland

[73] Assignee: Ciba-Geigy Corporation, Ardsley, N.Y.

[21] Appl. No.: 883,780

[22] Filed: Mar. 6, 1978

[30] Foreign Application Priority Data

Mar. 8, 1977 [CH] Switzerland .......................... 2869/77

[51] Int. Cl.$^2$ ............................................ C07D 213/57
[52] U.S. Cl. .................................................. 546/289
[58] Field of Search ...................... 260/294.5; 546/289

[56] References Cited

U.S. PATENT DOCUMENTS 2,790,806   4/1957   Middleton .......................... 260/294.9

OTHER PUBLICATIONS

Middleton, Chem. Abstracts, vol. 51, (19) p. 14,828f-g, Oct. 10, 1957.

Primary Examiner—Alan L. Rotman
Attorney, Agent, or Firm—Prabodh I. Almaula

[57] ABSTRACT

A process for the production of 2-bromo-3-cyano-4,6-diaminopyridine by cyclization of malodinitrile with hydrogen bromide, which comprises reacting malodinitrile in lower aliphatic hydrogenated hydrocarbons with hydrogen bromide used in an excess of 1 to 10% above the stoichiometric amount at temperatures of −10° C. to +30° C.

6 Claims, No Drawings

PROCESS FOR THE PRODUCTION OF 2-BROMO-3-CYANO-4,6-DIAMINOPYRIDINE

The present invention relates to an improved process for the production of 2-bromo-3-cyano-4,6-diaminopyridine by cyclisation of malodinitrile with hydrogen bromide and comprises reacting malodinitrile in lower halogenated hydrocarbons, especially chlorinated hydrocarbons, such as methylene chloride and ethylene chloride, as selective inert reaction medium, with hydrogen bromide used in an excess of 1 to 10% above the stoichiometric amount, at temperatures between −10° to +30° C., in order to obtain high yields. A reaction temperature of −10° to +10° C. is advantageously maintained during the introduction of hydrogen bromide and can then be raised to 10° to 30° C. when the reaction mixture is stirred. A particularly pure reaction product is obtained in this manner.

From the dimerisation of malodinitrile, 1,1,3-tricyano-2-aminopropene-1 is obtained as intermediate. This product does not need to be isolated and constitutes the actual cyclisation reagent which reacts with hydrogen bromide.

The process is in itself known. Conspicuous, however, are the relatively low yields, which are in the range of about 75%, based on the malodinitrile used in the reaction. The cause of the poor yields of 2-bromo-3-cyano-4,6-diaminopyridine is the formation of by-products, the amount of which is attributable to the large excess of hydrogen halide, the influence of the reaction medium and the high reaction temperature. Differences in the reaction temperature of even 10° C. affect the reaction course quite substantially.

It has now been found that, on carrying out the process of the present invention, the formation of by-products is reduced by five- to ten-fold in comparison to known processes in which an excess of about 35% of hydrogen bromide is used and the reaction medium consists of nitrobenzene or acetonitrile.

The advantages of the novel process are manifold. To name only a few: purer reaction products in higher yields of over 90%, a reaction medium which is easy to work with, a lower consumption of expensive hydrogen bromide resulting in a lower salt concentration in the waste waters, and, finally, higher space-time yields.

The reaction can be carried out for example as follows: Solid malodinitrile is dissolved in ethylene chloride. After cooling to about 5° C., hydrogen bromide in an excess of 5% over the stoichiometric amount is introduced, with stirring, in the course of 4 to 8 hours above the surface of the solution, whereupon the bromide precipitates. The reaction temperature is meanwhile allowed to rise from about −5° C. to about +5° C. When the introduction of hydrogen bromide is complete, the reaction mixture is stirred for 10 to 15 hours at 25° to 30° C.

For working up, the batch is poured onto ice-water and the ethylene chloride is distilled off under normal pressure. After cooling to 50° C, the batch is neutralised with about 30% sodium hydroxide solution, the precipitated product is filtered off after stirring for 1 hour at 50° C., washed with water and dried at 80° C.

The product is a valuable intermediate for the manufacture of dyes. By reaction for example with dyes which contain amino groups, valuable dyes are obtained.

The following Examples illustrate the invention, but imply no restriction to what is described therein.

EXAMPLE 1

A 250 ml Planschliff flask equipped with a glass anchor agitator, thermometer and pressure equaliser, is charged with 125.7 g (100 ml) of ≫99.5% ethylene chloride and 33 g (0.5 mole) of >98% malodinitrile, which gradually dissolves with stirring. The temperature falls from 20°–25° C. to 10°–15° C. When all the malodinitrile is dissolved, the solution is cooled to −5° C. under a weak flow of nitrogen. The flow of nitrogen is then stopped. A total of 42.5 g (0.525 mole) of ≫99.8% hydrogen bromide is introduced uniformly into the closed apparatus above the surface in the course of 6 hours at a stirring rate of ~150 rpm. As soon as the introduction of hydrogen bromide is complete, the reaction mixture is stirred for ½ hour at +5° C. The temperature is then allowed to rise slowly to 20° C. (about 1 hour). Stirring is then continued for 15 hours at 20° to 25° C.

Working up method 1

With stirring (100 rpm), the reaction mass is then poured into 150 ml of water of 0° C. in a 500 ml Planschiff flask. The mixture is heated, with stirring (150 rpm), and ethylene chloride is distilled off under normal pressure. After cooling to 50° C. (aqueous phase: pH 0.8 to 1), the fine suspension of the hydrobromide product is titrated, with stirring, with about 36 g (0.27 mole) of ≙ about 27 ml of 30% sodium hydroxide solution to a pH of 7 to 7.5 in the course of 20 to 30 minutes. After stirring for ¼ hour, the pH is adjusted if necessary to 7 to 7.5 with 30% sodium hydroxide solution. The precipitated product is then filtered off at 50° C. with a G3 glass suction filter (diameter 10 cm), washed with 6 equal portions of altogether 120 ml of warm water of 50° C., well filtered with suction, pressed, and dried at 80° C. in vacuo.

Yield: 50 to 50.5 (93 to 94% of theory, based on the malodinitrile).

The reaction product can also be worked up in a different manner:

Working up method 2

A total amount of 98 ml of ethylene chloride is distilled off direct from the reaction mixture at a bath temperature of about 40° C. and under an initial pressure of about 100 torr, towards the end of the distillation under about 25 torr (coil condenser in CO₂/methyl cellosolve, −40° C.). The solvent-free residue is suspended in 200 ml of water in a 500 ml Planschiff flask with strring and at 50° C. adjusted to pH 7 to 7.5 with about 25 ml of 30% sodium hydroxide solution. After stirring for ¼ hour, the pH is adjusted to 7 to 7.5 with sodium hydroxide solution if necessary. The precipitated product is filtered off at 50° C. with a G3 glass suction filter and washed with 6 equal portions of altogether 120 ml of warm water, well filtered with suction and dried in vacuo at 80° C.

Yield dry: as in method 1.

Working up method 3

With stirring (100 rpm), the reaction mass is poured into 150 ml of water of 0° C. in a 500 ml Planschiff flask. The mixture is heated, with stirring, to 50° C. and adjusted to pH 7 to 7.5 with about 37 g (0.28 mole, 28 ml) of 30% sodium hydroxide solution. The mixture is further heated with slow stirring (50 rpm) and ethylene chloride is distilled off under normal pressure (bath temperature 100° C., distillation temperature 72° C.). Towards the end of the distillation, the bath temperature is brought to 130° C. When the distillation temperature has reached about 85° C., the heating bath is removed.

Distillate: about 100 ml of ethylene chloride about 10 ml of water.

After cooling to 50° C., the batch is stirred for 1 hour at 50° C. The precipitated product is filtered off at 50° C. with a G3 glass suction filter and the filter cake is washed with 6 equal portions of altogether 120 ml of warm water of 50° C., well filtered with suction, pressed, and dried at 80° C. in vacuo.

Yield dry: as in method 1.

Working up method 4

The reaction mixture is cooled to 10° C. In the course of 2 hours about 4.6 g (0.27 mole) of 100% ammonia is introduced into the closed apparatus above the surface. Then a total amount of 95 to 98 ml of ethylene chloride is distilled off at a bath temperature of about 40° C. and under an initial pressure of 100 torr, towards the end of the distillation under 20 torr (coil condenser in $CO_2$/-methyl cellosolve, −40° C.). 200 ml of water are added and the pH is adjusted to 6 with conc. ammonia, if desired. The suspension is heated to 70° C. and kept for 1 hour at this temperature, then filtered at 70° C. with a G3 glass suction filter. The filter cake is washed with 6 equal portions of altogether 120 ml of water, well filtered with suction, pressed, and dried in vacuo.

Yield: 47 to 47.5 g (90 to 91% of theory, based on the malodinitrile).

EXAMPLE 2

The procedure described in Example 1 is repeated, except that equivalent amounts of methylene chloride are used instead of ethylene chloride, affording a crude yield of 51.2 g (96% of theory, based on the malodinitrile) of 2-bromo-3-cyano-4,6-diaminopyridine.

What is claimed is:

1. An improved process for the production of 2-bromo-3-cyano-4,6-diaminopyridine by cyclisation of malodinitrile with hydrogen bromide, which comprises reacting malodinitrile in lower aliphatic hydrogenated hydrocarbons with hydrogen bromide used in an excess of 1 to 10% above the stoichiometric amount at temperature of −10° C. to +30° C.

2. A process as claimed in claim 1, wherein the reaction is carried out in aliphatic chlorinated hydrocarbons.

3. A process as claimed in claim 1, wherein the reaction is carried out in methylene chloride or ethylene chloride.

4. A process as claimed in claim 1, wherein the reaction is carried out in ethylene chloride.

5. A process as claimed in claim 1, wherein hydrogen bromide is introduced at temperatures of −10° C. to +10° C.

6. The 2-bromo-3-cyano-4,6-diaminopyridine produced by the process as claimed in claim 1.

* * * * *